(12) United States Patent
Selman et al.

(10) Patent No.: US 8,988,082 B2
(45) Date of Patent: Mar. 24, 2015

(54) BIOMASS MONITOR PROBES AND BIOREACTORS INCORPORATING SUCH PROBES

(75) Inventors: Jonathan Selman, Powys (GB); John Carvell, Ceredigion (GB)

(73) Assignee: Aber Instruments Limited, Aberystwyth (GB)

( * ) Notice: Subject to any disclaimer, the term of this patent is extended or adjusted under 35 U.S.C. 154(b) by 927 days.

(21) Appl. No.: 13/091,263

(22) Filed: Apr. 21, 2011

(65) Prior Publication Data

US 2011/0260738 A1 Oct. 27, 2011

(30) Foreign Application Priority Data

Apr. 23, 2010 (GB) .................................. 1006793.2

(51) Int. Cl.
*G01R 27/28* (2006.01)
*G01N 33/487* (2006.01)
*C12M 1/34* (2006.01)

(52) U.S. Cl.
CPC ......... *G01N 33/48735* (2013.01); *C12M 41/36* (2013.01)
USPC ............................ 324/649; 324/600; 324/612

(58) Field of Classification Search
USPC .................. 324/649, 663–682, 765
See application file for complete search history.

(56) References Cited

U.S. PATENT DOCUMENTS

| 4,810,650 A | 3/1989 | Kell et al. |
| 6,596,507 B2 | 7/2003 | Ossart |
| 2005/0239198 A1 | 10/2005 | Kunas et al. |
| 2011/0316563 A1* | 12/2011 | Davies et al. ................. 324/663 |

FOREIGN PATENT DOCUMENTS

| DE | 3824154 A1 | 1/1990 |
| EP | 1046905 A1 | 10/2000 |
| EP | 1138758 A1 | 10/2001 |
| GB | 2465282 A | 5/2010 |
| WO | WO2006116069 A1 | 11/2006 |
| WO | WO2010010313 A2 | 1/2010 |

* cited by examiner

*Primary Examiner* — Melissa Koval
*Assistant Examiner* — Trung Nguyen
(74) *Attorney, Agent, or Firm* — Gordon & Jacobson, PC

(57) ABSTRACT

A bioreactor includes a plastic enclosure for containing a biological medium, the enclosure being integrally formed to have one or more elongate port extensions projecting outwardly from the enclosure and communicating from the exterior to the interior of the enclosure. A biomass impendence monitor probe is provided for use in conjunction with the bioreactor. The probe is pushed into one or more of the elongate ports in order to have an electrode arrangement positioned internally of the container. The probe has an elongate housing having an outer surface extending along and contiguous with the elongate inner surface of the port extension. The housing extends from the electrode end of the probe to a remote end. The housing is provided with an electrical connector connected to the electrode arrangement.

18 Claims, 2 Drawing Sheets

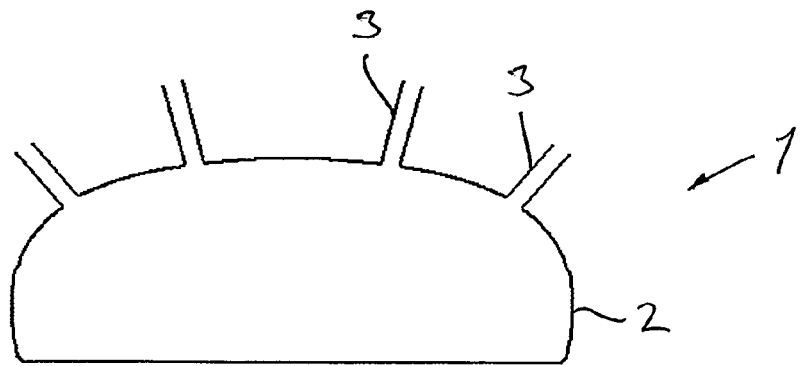
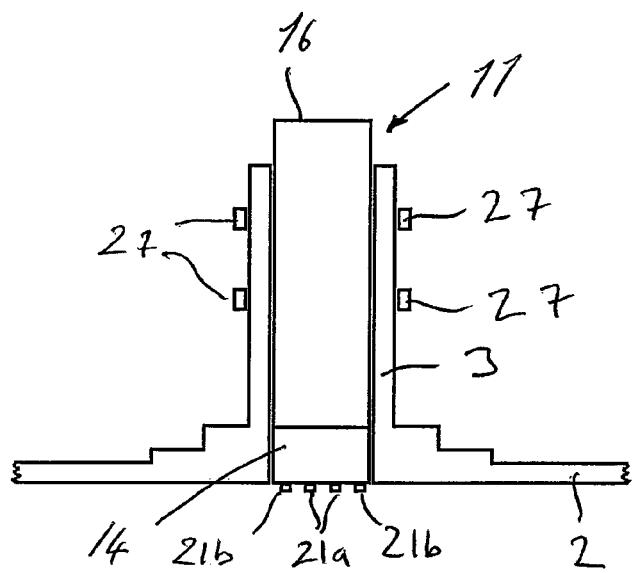
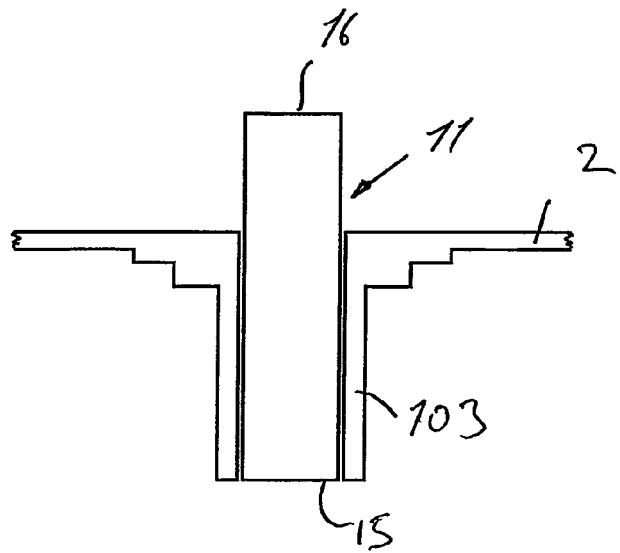

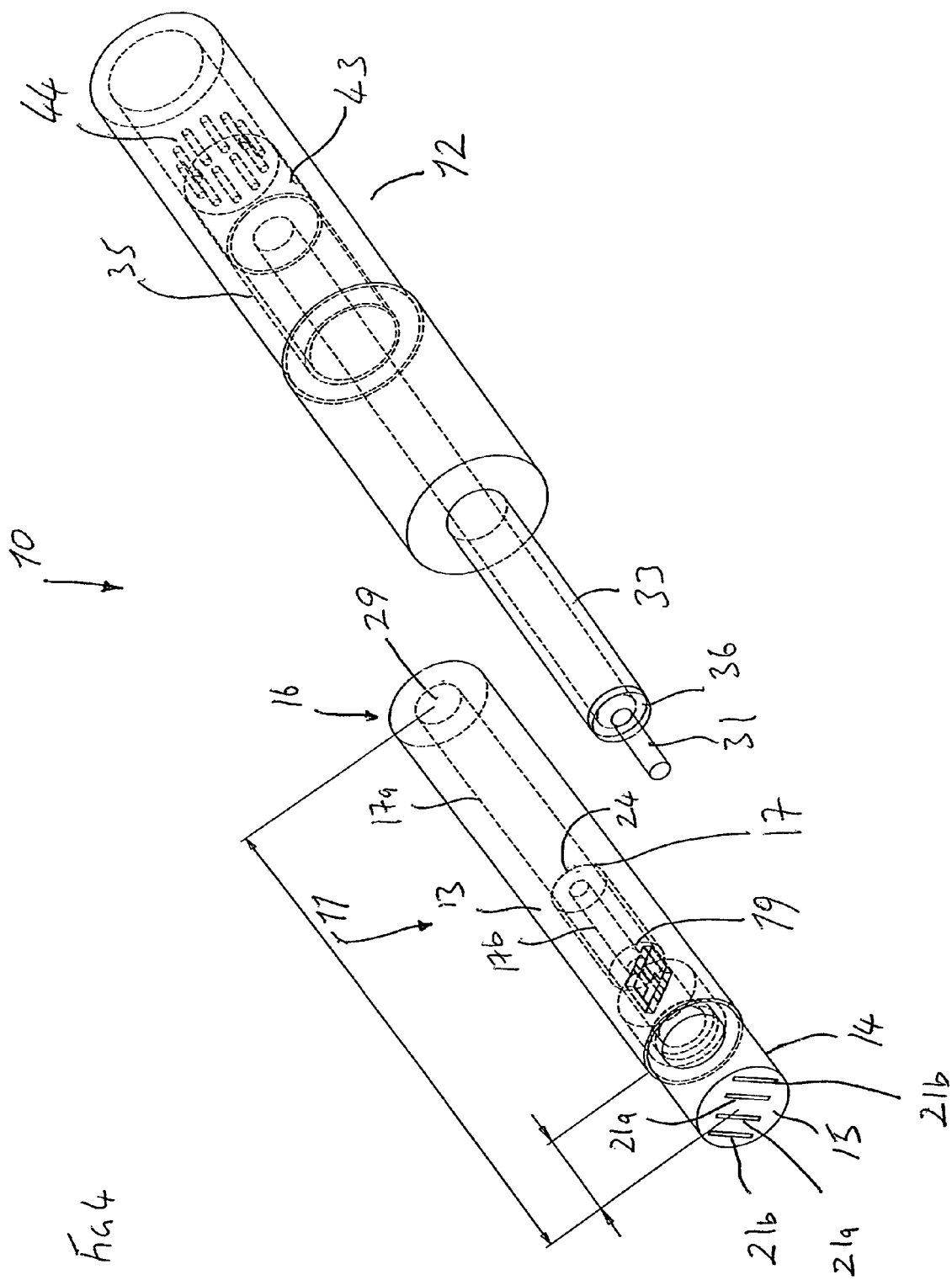

BIOMASS MONITOR PROBES AND BIOREACTORS INCORPORATING SUCH PROBES

CROSS-REFERENCE TO RELATED APPLICATION

This application claims priority from GB 1006793.2, filed Apr. 23, 2010, which is hereby incorporated by reference herein in its entirety.

BACKGROUND OF THE INVENTION

1. Field of the Invention

The present invention relates to biomass monitor probes and bioreactors incorporating such probes. The invention relates particularly to probes intended for use as single use monitor probes and bioreactors.

2. State of the Art

Different embodiments of single use biomass monitor probes, devices and bioreactors incorporating such probes are disclosed in, for example, WO2010/010313. An improved arrangement has now been devised.

SUMMARY OF THE INVENTION

According to a first aspect of the present invention, there is provided a bioreactor arrangement comprising:
  i) an enclosure for containing a biological medium and including one or more elongate port extensions projecting outwardly from the enclosure and communicating from the exterior to the interior of the enclosure;
  ii) an impedance monitor probe being secured in one or more of the elongate ports in order to have an electrode arrangement positioned to monitor the biological medium, the impedance monitoring probe comprising an elongate housing having an outer surface extending along and contiguous with the elongate inner surface of the port extension, the housing extending from the electrode end of the probe to a remote end, the remote end being provided with an opening of a bore which extends at least part-way internally along the length of the elongate housing to an electrical connector connected to the electrode arrangement.

It is preferred that the port extension comprises a cylindrical port extension.

In one realisation of the invention, the monitor probe is positioned to have the electrode arrangement positioned internally of the enclosure.

In one embodiment, it is preferred that the enclosure for containing the biological medium comprises a flexible bag, pouch or wall and the one or more elongate cylindrical port extensions projecting outwardly from the container are formed integrally with the enclosure.

It is preferred that the elongate housing of the impedance monitor probe extends along the majority of the length of the elongate port extension. This provides for secure location in the port extension. Beneficially, the impedance monitor probe is pushed fitted into position in the one or more of the elongate ports, preferably via the external open end of the respective elongate port. This means that access for securing the probe in position is required from externally only of the bioreactor. There is no need to access the reactor from internally to fit the probe in position. Ties, clamps or other securing means may be applied to the exterior of the port extension in order to secure the engagement between the push fitted probe and the port extension.

Preferably the elongate housing extends beyond the outer end of the elongate port extension. This provides for convenient connection of the probe to other components.

Preferably, the impedance monitor probe of the bioreactor arrangement is formed of at least two-parts comprising a probe part and a connector part arranged to connect with the probe part, the connector part having an elongate proximal end part arranged to be inserted into the bore in the probe so as to facilitate electrical connection with the electrode arrangement; and a distal end housing part containing monitoring circuitry and/or electronic signal conditioning or processing means enabling a signal conditioning or processing operation to be conducted on the electrical signal from the probe.

According to a further aspect, the present invention provides an impedance monitoring probe part having a measurement electrode arrangement positioned at an end of the probe part, and comprising an elongate housing extending from the electrode end of the probe part to a remote end, the remote end being provided with an opening of a bore cavity which extends at least part-way internally along the length of the elongate housing to an electrical connector connected to the electrode arrangement.

The probe part housing is beneficially made of a plastics material that is sterilisable with the bioreactor and disposable.

It is preferred that the electrical connector is positioned at the end of the internal bore in the probe part housing. Beneficially, the electrical connector is positioned closer to the electrode end of the probe part than to the remote end. Most preferably, the electrical connector is positioned proximate the electrode end of the probe part.

Positioning the electrical connector closely adjacent to the electrode arrangement provides enhanced technical performance because it reduces the size of the electrical circuit in the disposable probe part. This is important because of calibration issues. Ideally, the circuitry in each probe part for connection to an electrical connector part (as described below) will be repeatably identical. Differences in the circuitry between different probe parts connected to the same connector, one after the other, can result in calibration issues. By keeping the monitoring circuitry in the disposable probe part to a minimum, the calibration issues are minimised because the major part of the monitoring circuitry is provided within the connector part of the two part probe.

A further advantage is that, by keeping the amount of circuitry in the probe part to a minimum, the shadow cast by the metallic circuitry during gamma irradiation sterilisation is kept to a minimum. Additionally the cost of the probe part is also kept to a minimum.

In one embodiment, it is preferred that the electrical connector comprises one part of a male/female socket and pin electrical connector, preferably the socket part of a socket and pin electrical connector.

According to a further aspect, the present invention provides a two-part, impedance monitoring device comprising a single use disposable impedance monitoring probe as defined herein and in the appended claims; and a re-usable connector part arranged to connect with the disposable probe, the connector part having an elongate proximal end part arranged to be inserted into the bore in the probe so as to facilitate electrical connection with the electrode arrangement; and a distal end housing part containing an electrical circuit and/or electronic signal conditioning or processing means enabling a signal conditioning or processing operation to be conducted on the electrical signal from the probe.

In a preferred embodiment, the electronic signal conditioning or processing means provided in the distal end housing part comprises a pre-amplifier.

It is preferred that the connector part elongate proximal end part extends along substantially the entire length of the bore in the probe in order to facilitate electrical connection with the electrode arrangement of the probe.

According to a further aspect, the invention provides a bioreactor arrangement comprising:
i) a flexible plastics enclosure for containing a biological medium the enclosure being integrally formed to have one or more elongate port extensions, projecting outwardly from the enclosure and communicating from the exterior to the interior of the enclosure;
ii) an impedance monitor probe being pushed into one or more of the elongate ports in order to have an electrode arrangement positioned internally of the container, the impedance monitoring probe comprising an elongate plastics housing having an outer surface extending along and contiguous with the elongate inner surface of the cylindrical port extension, the housing extending from the electrode end of the probe to a remote end, the elongate housing being provided with an electrical connector connected to the electrode arrangement.

It is generally preferred that the bioreactor is sterilised with the impedance monitor probe already pushed into position in the one or more of the elongate ports.

The invention will now be further described in specific embodiments, by way of example only and with reference to the accompanying drawings.

BRIEF DESCRIPTION OF THE DRAWINGS

FIG. 1 is a schematic view of a bioreactor enclosure for use in performance of the invention.

FIG. 2 is a schematic side view of an impedance monitor probe positioned in the bioreactor of FIG. 1.

FIG. 3 is a schematic view similar to the view of FIG. 2 of an impedance monitor probe positioned in an alternative embodiment of bioreactor.

FIG. 4 is a perspective view of the two part impedance monitoring device (including the probe of the preceding figures).

DETAILED DESCRIPTION OF THE PREFERRED EMBODIMENTS

Referring to the drawings, and initially to FIG. 1, there is shown a bioreactor 1 comprising a flexible plastics enclosure 2 typically in the form of a container or bag. Such bioreactors are known in the art to be used as single use bioreactors for use in fermentation, brewing or other biological processes. The flexible plastics enclosure 2 is typically gamma irradiated prior to use in order to sterilise the bioreactor. The bioreactor is typically disposed of following a single use and accordingly it is important to minimise the manufacturing and component costs of the product.

The container is provided with a series of elongate tube ports 3, integrally formed with the enclosure and, in the embodiments of FIGS. 1 and 2, projecting to extend outwardly from the wall of the enclosure 2.

A two-part impedance monitoring device 10 is shown in FIG. 4. The monitoring device comprises a disposable probe part 11 and a connector part 12. The disposable probe part 11 and re-usable connector part 12 are separable in service (i.e. after manufacture of the probe the probe part and the connector part can be separated). The disposable probe part 11 is in use arranged to be push fitted into a tube port 3 in the bioreactor enclosure 2 prior to sterilisation irradiation.

The probe part 11 has an electrode end 14 which is inserted into the bioreactor via the tube port 3 to be in contact with the culture in the bioreactor containing living cells (the biomass medium). The electrode end 14 includes an end surface 15 on which are mounted 2 pairs of platinum electrodes, which are formed as elongate strips at the distal end of the probe as shown most clearly in FIG. 4. The outer electrodes 21b are used to pass current through the biomass media. The inner electrodes 21a are used to sense the voltage across the gap between them. This arrangement is preferred over a simple 2 electrode arrangement in order to reduce the effect of polarisation that occurs at the current electrodes 21b. A radio frequency (RF) electric current is applied to the biomass solution via the current electrodes 21b, and the resultant voltage and current are sensed by the sensing electrodes 2a.

In this impedance measurement technique, the voltage and current measurements obtained, an appropriate processor is able to determine the capacitance (pF) and conductance (mS) of the solution. These values are then scaled using the known probe characteristics to give conductivity (mS/cm) and capacitance (pF/cm). Capacitance (pF/cm) is proportionally related to the permitivity of the solution. The (RF) electric current is applied via the current electrodes 21b, and the resultant voltage and current sensed by the sensing electrodes 21a. Using the voltage and current measurements obtained, an appropriate processor is able to determine the capacitance (pF) and conductance (mS) of the solution. This impedance measurement technique is known in the art and described in, for example U.S. Pat. No. 4,810,650.

The probe part 11 has an elongate housing 13 extending away from the electrode end 14. The length of the probe part housing 13 is preferably such that, with the disposable probe part 11 retained in the tube port 3 of the bioreactor enclosure 2, the distal end 16 of the probe part housing 13 is positioned outwardly beyond the end of tube port 3. This makes connection with the connector part 12 more convenient. The internal diameter of the tube port 3 and the external diameter of the probe part housing 13 are matched such that the probe part is a secure push fit into the tube port 3 which resiliently grips the probe part housing 13. This connection is enhanced because of the relatively long length of the tube port and the probe housing. This feature also means that the probe part 11 is stably mounted with respect to the bioreactor enclosure 2. Plastic ties or clamps 27 may be used to enhance the securing of the probe part housing 13 in the tube port 3.

The probe part 11 is push fitted into the respective tube port 13 from externally of the enclosure. This means that access to the interior of the enclosure is not required to fit the probe part into the tube port 13.

The interior of the probe part housing 13 is provided with an internal bore 17 extending from an opening 29 in the distal end 16 of the probe part 11 internally along the length of the elongate housing 13 to an electrical connector 19 connected to the electrode arrangement. The internal bore has a relatively large diameter portion 17a stepping down to a relatively narrower diameter portion 17b which comprises an electrical connector socket arranged to connect with an electrical connector pin 31 provided on the connector part 12. In this way, even though the probe part 11 is relatively long and electrically connected to the connector part 12, the location of electrical connection is close to the electrode arrangement which gives improved measurement performance.

The reason for this is that such an arrangement minimises the size of the electrical circuit in the disposable probe part 11 thereby minimising stray impedances which contribute system to errors. This is important because of calibration issues. Ideally, the circuitry in each probe part 11 for connection to the connector part 12 will be repeatably identical. Differences in the circuitry between different probe parts connected to the same connector, one after the other, can result in calibration issues. By keeping the monitoring circuitry in the disposable probe part 11 to a minimum, the calibration issues are minimised because the major part of the monitoring circuitry is provided within the connector part 12 of the two part device. A further advantage is that, by keeping the amount of circuitry in the probe part 11 to a minimum, the shadow cast by the metallic circuitry during gamma irradiation sterilisation is kept to a minimum. Additionally the cost of the probe part 11 is also kept to a minimum.

The pin connector 31 of the connector part is provided at the end of an elongate proximal end part 33 which is shaped and dimensioned to be a snug sliding fit into the internal bore 17a of the probe part 11. The shoulder 36 abuts against the seat 24 when the elongate proximal end part 33 of the connector part 12 is fully inserted home into the bore in the probe part 11. This provides good rigidity and support between the probe part 11 and the connector part 12. The distal part of the connector part 12 has an increased diameter housing part 35 and an internal cavity 43 which contains monitoring circuitry and typically signal processing electronics for carrying out initial signal conditioning or processing on the signal derived from the electrode arrangement. The end of the connector part 12 is provided with a proprietary socket/pin connector 44 for connection to a signal pre-amplifier (not shown connected).

The arrangement provides that the probe part 11 can be inserted into the tube port 3 prior to sterilisation and that it is easy to subsequently connect and disconnect the connector part 12 of the device. Separating the connection part 12 from the probe part 11 prior to sterilisation, and removing the bulk of the circuitry, minimises the risk of gamma radiation not reaching all parts of the probe part 11 in the sterilisation process. Therefore the probe part 11 and connector part 12 are separable in service. Consequently, the probe part 11 can be constructed to be single use and disposable with the bioreactor enclosure. The probe part 11 is manufactured of suitable materials such a plastics materials and the more expensive signal processing components are housed in the re-usable connector part 12.

FIG. 3 shows an alternative embodiment of a bioreactor in which the tube port 103 projects internally of the enclosure 2. The probe part 11 is once again push fitted into the tube port 3 from externally of the enclosure 2.

Advantageously, the bioreactor arrangement includes a two part arrangement, a monitoring probe part 11 and a connector part 12, arranged such that the probe part 11 can be inserted into the tube port of a bioreactor whilst still enabling the connector part to be separated from the probe part. The circuitry in the probe part 11 is arranged to be minimal such that on removal of the connector the risk of gamma radiation not reaching all parts of the probe in the sterilisation process is minimised.

It will be readily appreciated that the embodiments described are explanatory only and other arrangements falling within the scope of the invention are envisaged. For example the electrodes provided on the external face could be replaced by concentric band electrodes positioned about the end of the probe part.

What is claimed is:

1. A bioreactor arrangement comprising:
   i) an enclosure for containing a biological medium, and including one or more elongate port extensions projecting outwardly from the enclosure and communicating from the exterior to the interior of the enclosure; and
   ii) an impedance monitor probe being secured in one or more of the elongate ports in order to have an electrode arrangement positioned for monitoring of the medium in the enclosure, the impedance monitoring probe comprising an elongate housing having an outer surface extending along and contiguous with the elongate inner surface of the port extension, the housing extending from the electrode end of the probe to a remote end, the remote end being provided with an opening of a bore which extends at least part-way internally along the length of the elongate housing to an electrical connector connected to the electrode arrangement, wherein the electrical connector is positioned in the bore of the housing and is closer to the electrode end of the probe than to the remote end.

2. A bioreactor arrangement according to claim 1, wherein the enclosure for containing the biological medium comprises a flexible bag, pouch or wall and the one or more elongate port extensions projecting outwardly from the container are formed integrally with the enclosure.

3. A bioreactor arrangement according to claim 1, wherein the elongate housing of the impedance monitor probe extends along the majority of the length of the elongate port extension.

4. A bioreactor arrangement according to claim 3, wherein the elongate housing extends beyond the outer end of the elongate port extension.

5. A bioreactor arrangement according to claim 1 wherein, the impedance monitor probe is formed of at least two-parts comprising a probe part and a connector part arranged to connect with the probe part, the connector part having an elongate proximal end part arranged to be inserted into the bore in the probe so as to facilitate electrical connection with the electrode arrangement; and a distal end housing part containing at least one of monitoring circuitry and electronic signal conditioning or processing means enabling a signal conditioning or processing operation to be conducted on the electrical signal from the probe.

6. A bioreactor arrangement according to claim 1, wherein the electrical connector is positioned at the electrode end of the probe.

7. A bioreactor arrangement according to claim 1, wherein the electrical connector comprises one part of a socket and plug electrical connector.

8. A bioreactor arrangement according to claim 1, wherein the electrical connector comprises the socket part of the socket and plug electrical connector.

9. An arrangement comprising:
   an enclosure for containing a biological medium; and
   an impedance monitoring probe having a measurement electrode arrangement positioned at an end of the probe for monitoring of the medium in the enclosure, the probe comprising an elongate housing extending from the electrode end of the probe to a remote end, the remote end being provided with an opening of a bore which extends at least part-way internally along the length of the elongate housing to an electrical connector connected to the electrode arrangement, wherein the electrical connector is positioned in the bore of the housing and is closer to the electrode end of the probe than to the remote end.

10. An arrangement according to claim 9, wherein the electrical connector is positioned at the electrode end of the probe.

11. An arrangement according to claim 9, wherein the electrical connector comprises one part of a socket and plug electrical connector.

12. An arrangement according to claim 9, wherein the electrical connector comprises the socket part of the socket and plug electrical connector.

13. An arrangement according to claim 9, further comprising a connector part arranged to connect with the probe, the connector part having an elongate proximal end part arranged to be inserted into the bore cavity in the probe so as to facilitate electrical connection with the electrode arrangement; and a distal end housing part containing at least one of monitoring circuitry and electronic signal conditioning or processing means enabling a signal conditioning or processing operation to be conducted on the electrical signal from the probe.

14. An arrangement according to claim 13, wherein the electronic signal conditioning or processing means provided in the distal end housing part comprises a pre-amplifier.

15. An arrangement according to claim 13, wherein the elongate proximal end part of the connector part extends along substantially the entire length of the bore cavity in the probe in order to facilitate electrical connection with the electrode arrangement of the probe.

16. A bioreactor arrangement comprising:
  i) a flexible plastics enclosure for containing a biological medium the enclosure being integrally formed to have one or more elongate port extensions, projecting outwardly from the enclosure and communicating from the exterior to the interior of the enclosure; and
  ii) an impedance monitor probe being pushed into one or more of the elongate ports in order to have an electrode arrangement positioned for monitoring the biological medium, the impedance monitoring probe comprising an elongate plastics housing having an outer surface extending along and contiguous with the elongate inner surface of the port extension, the housing extending from the electrode end of the probe to a remote end, the remote end being provided with an opening of a bore which extends at least part-way internally along the length of the elongate housing to an electrical connector connected to the electrode arrangement, wherein the electrical connector is positioned in the bore of the housing and is closer to the electrode end of the probe than to the remote end.

17. A bioreactor according to claim 16, wherein the bioreactor is sterilised with the impedance monitor probe already pushed into position in the one or more of the elongate ports.

18. A bioreactor according to claim 16, wherein the impedance monitor probe is pushed into position in the one or more of the elongate ports via the external open end of the respective elongate port.

* * * * *